(12) United States Patent
Funke et al.

(10) Patent No.: US 7,497,931 B2
(45) Date of Patent: Mar. 3, 2009

(54) DISTILLATIVE PREPARATION OF IPDA HAVING A HIGH CIS/TRANS ISOMER RATIO

(75) Inventors: Frank Funke, Ludwigshafen (DE); Thomas Hill, Ludwigshafen (DE); Jobst Rüdiger Von Watzdorf, Mannheim (DE); Wolfgang Mattmann, Limburgerhof (DE); Wolfgang Harder, Weinheim (DE); Erhard Henkes, Einhausen (DE); Gerd Littmann, Weinheim (DE); Manfred Julius, Limburgerhof (DE)

(73) Assignee: BASF Aktiengesellschaft (DE)

( * ) Notice: Subject to any disclaimer, the term of this patent is extended or adjusted under 35 U.S.C. 154(b) by 761 days.

(21) Appl. No.: 10/524,084

(22) PCT Filed: Aug. 8, 2003

(86) PCT No.: PCT/EP03/08831
§ 371 (c)(1),
(2), (4) Date: Feb. 9, 2005

(87) PCT Pub. No.: WO2004/024668
PCT Pub. Date: Mar. 25, 2004

(65) Prior Publication Data
US 2005/0252761 A1    Nov. 17, 2005

(30) Foreign Application Priority Data
Aug. 9, 2002    (DE) ................ 102 36 674

(51) Int. Cl.
*B01D 3/14* (2006.01)
*C07C 209/84* (2006.01)
*C07C 209/86* (2006.01)

(52) U.S. Cl. .......... 203/1; 203/2; 203/73; 203/99; 203/DIG. 19; 564/497

(58) Field of Classification Search ............ 203/1, 203/2, 73, 99, DIG. 19; 564/497, 499
See application file for complete search history.

(56) References Cited

U.S. PATENT DOCUMENTS
5,373,068 A    12/1994    Piana et al.
(Continued)

FOREIGN PATENT DOCUMENTS
DE        42 11 454    10/1993
(Continued)

*Primary Examiner*—Virginia Manoharan
(74) *Attorney, Agent, or Firm*—Connolly Bove Lodge & Hutz LLP

(57) ABSTRACT

The invention relates to a process for recovering 3-aminomethyl-3,5,5-trim-ethylcyclohexylamine (isophoronediamine, IPDA) having a fractionally distilled cis/trans isomer ratio of at least 73/27. The process includes the following steps:
  a) providing IPDA in a cis/trans isomer ratio of <73/27;
  b) feeding IPDA into the middle region of a distillation column having internals and distilling the IPDA in this distillation column at a temperature of from 5 to 300.degree. C. and a pressure of from 10 to 2000 mbar;
  c) optionally further distilling the IPDA obtained by step b) in at least one further column, and thus further purifying the IPDA;
where steps b) and optionally c) separate the IPDA used in step a) into at least five fractions ia) to iv):
  ia) the organic proportion of a fraction of impurities having lower boiling points than tans-IPDA,
  ib) the aqueous proportion of a fraction of impurities having lower boiling points than trans-IPDA,
  ii) a fraction of impurities having higher boiling points than cis-IPDA,
  v) an IPDA fraction having a cis/trans isomer ratio of $\geq 73/27$ and
  vi) a depleted IPDA fraction having a cis/trans isomer ratio of $\leq 66/34$.

18 Claims, 7 Drawing Sheets

U.S. PATENT DOCUMENTS

| | | |
|---|---|---|
| 5,504,254 A | 4/1996 | Haas et al. |
| 5,583,260 A | 12/1996 | Haas et al. |
| 5,756,845 A | 5/1998 | Voit et al. |
| 6,022,999 A | 2/2000 | Voit et al. |
| 7,256,313 B2 * | 8/2007 | Funke et al. ............... 564/448 |
| 2004/0225156 A1 | 11/2004 | Funke et al. |

FOREIGN PATENT DOCUMENTS

| | | |
|---|---|---|
| DE | 43 43 890 | 6/1995 |
| DE | 43 43 891 | 6/1995 |
| DE | 101 42 635 | 3/2003 |
| EP | 0 729 937 | 9/1996 |
| EP | 0 926 130 | 6/1999 |

* cited by examiner

DISTILLATIVE PREPARATION OF IPDA HAVING A HIGH CIS/TRANS ISOMER RATIO

RELATED APPLICATIONS

This application is a national stage application (under 35. U.S.C. 371) of PCT/EP2003/008831 filed Aug. 8, 2003, which claims benefit to German application number 102 36 674.8 filed Aug. 9, 2002.

The invention relates to distillative processes for preparing 3-aminomethyl-3,5,5-trimethyl-cyclohexylamine (isophoronediamine, IPDA) having a high cis/trans isomer ratio.

IPDA is used as a starting product for preparing isophorone diisocyanate (IPDI), an isocyanate component for polyurethane systems, as an amine component for polyamides and as a hardener for epoxy resins. IPDA is customarily prepared from 3-cyano-3,5,5-trimethylcyclohexanone (isophoronenitrile, IPN) by converting the carbonyl group to an amino group and the nitrile group to an aminomethyl group in the presence of ammonia, hydrogen and customary hydrogenation catalysts. Mixtures of cis-IPDA and trans-IPDA are obtained. Both isomers have different reactivities which is of significance for the intended technical application. According to DE-A 42 11 454, the use of an IPDA isomer mixture consisting of more than 40% of the trans-isomer and less than 60% of the cis-isomer as a reaction component in polyaddition resins, especially epoxy resins, both lengthens the pot life and lowers the maximum curing temperature. Conversely, to achieve a very high reaction rate, preference is given to IPDA isomer mixtures which have a very high content of the cis-isomer ($\geq$70%). Commercially obtainable IPDA therefore has a cis/trans isomer ratio of 75/25.

Various processes for achieving a high cis/trans or high trans/cis ratio are already known from the prior art.

According to DE-A 43 43 890, the aminating hydrogenation of IPN to IPDA is effected by allowing a mixture of IPN, ammonia and a $C_1$-$C_3$-alcohol to trickle through a trickle bed reactor equipped with a cobalt and/or ruthenium fixed bed catalyst in the presence of hydrogen at from 3 to 8 MPa and a temperature of from 40 to 150° C., preferably from 90 to 130° C., and working up the reaction mixture distillatively to remove $NH_3$, $H_2O$ and by-products. When a supported Ru catalyst is used, high cis/trans isomer ratios of 84/16 (overall yield of IPDA: 81%) are achieved.

DE-A 43 43 891 describes a process for preparing IPDA by reacting IPN with hydrogen at a pressure of from 3 to 20 MPa and a temperature of up to 150° C. in the presence of ammonia and a suspension or fixed bed hydrogenation catalyst from the group of cobalt, nickel and noble metal catalysts, and working up the resulting reaction mixture distillatively. The reaction is carried out in two stages and precisely defined temperature ranges have to be maintained for the individual stages. A cis/trans isomer ratio of 80/20 can be achieved in an overall IPDA yield of 91.9%.

In the process of EP-A 0 926 130, the hydrogenation is carried out in the presence of an acid over catalysts which comprise copper and/or a metal of the eighth transition group of the Periodic Table. Either Lewis or Brönstedt acids are used; preference is given to using 2-ethylhexanoic acid. The addition of acid has the effect of increasing the cis/trans isomer ratio. The cis/trans isomer ratios are generally $\geq$70/30 at an overall IPDA yield of $\geq$90%.

The process of EP-B 0 729 937 is characterized in that the process is carried out in three spatially separated reaction chambers, and cobalt, nickel ruthenium and/or other noble metal catalysts are used. Upstream of the second reactor, aqueous NaOH solution is metered in, which reduces the formation of cyclic by-products such as 1,3,3-trimethyl-6-azabicyclo[3,2,1]octane.

In the process of DE-A 101 42 635.6, which has an earlier priority date but was unpublished at the priority date of the present invention, IPDA is obtained with a cis/trans isomer ratio of at least 70/30 starting from IPN by using a hydrogenation catalyst having an alkali metal content of $\leq$0.03% by weight, calculated as the alkali metal oxide, in the hydrogenation step.

A disadvantage of the existing processes for preparing IPDA with a high cis content is the costly and inconvenient preparation of the catalysts used. In addition, these catalysts generally suffer from aging which reduces their catalytic activity in the course of time. In order to compensate for this, the reaction temperature is usually increased which, however, leads to a deterioration in the cis/trans isomer ratio and the selectivity, and therefore to an increase in the formation of by-products. Most of the processes known from the prior art are notable for a complicated reaction procedure.

A process for preparing isophoronediamine having a high trans/cis isomer ratio can be taken from DE-A 42 11 454. In this process, trans-isophoronediamine can be prepared from isophoronenitrile via isophoronenitrilazine. It is also described that trans-isophoronediamine could be obtained by distilling commercially available cis/trans isomer mixture. However, since the cis-isomer occurs as the main product, this process is uneconomic. No information is given on the apparatus used in the distillation.

It is an object of the present invention to provide a process for preparing isophoronediamine (IPDA) having a cis/trans isomer ratio of at least 73/27 which avoids the disadvantages of the prior art.

We have found that this object is achieved by a process for recovering 3-aminomethyl-3,5,5-trimethylcyclohexylamine (isophoronediamine, IPDA) having a cis/trans isomer ratio of at least 73/27 by fractional distillation, which comprises the following steps:

a) providing IPDA in a cis/trans isomer ratio of <73/27;
b) feeding IPDA into the middle region of a distillation column having internals and distilling the IPDA in this distillation column at a temperature of from 5 to 300° C. and a pressure of from 10 to 2000 mbar;
c) optionally further purifying the IPDA obtained by step b) by distilling in at least one further column;

where steps b) and c) separate the IPDA used in step a) into at least five fractions ia) to iv):

ia) the organic proportion of a fraction of impurities having lower boiling points than trans-IPDA,
ib) the aqueous proportion of a fraction of impurities having lower boiling points than trans-IPDA,
ii) a fraction of impurities having higher boiling points than cis-IPDA,
iii) an IPDA fraction having a cis/trans isomer ratio of $\geq$73/27 and
iv) an IPDA fraction having a cis/trans isomer ratio of $\leq$66/34.

In principle, the process according to the invention allows IPDA to be obtained, starting from IPDA having any desired cis/trans isomer ratio, in a defined, constant cis/trans isomer ratio, and a high cis content which can be specified in accordance with the application can be set in a defined manner. The process is thus substantially independent of the given cis/trans isomer ratio and also remains economic when aging of the catalyst and an associated increase in the reaction temperature reduce the cis content in the IPDA in the course of time. The process according to the invention is particularly economical when IPDA is obtained with a cis/trans isomer ratio of $\geq 73/27$ from IPDA having a cis/trans isomer ratio of $<73/27$.

Fraction ib) is wastewater occurring in the process according to the invention which requires treatment. The proportion of IPDA in the fraction ib) obtained by steps b) and c) is generally $\leq 2\%$ by weight, preferably $\leq 1000$ ppm, more preferably $\leq 200\%$ ppm, based on the total weight of the fraction ib).

The individual steps of the process are now further illustrated hereinbelow.

Step a)

The process according to the invention allows in particular IPDA to be obtained in which the impurity content is less than 2% by weight, preferably less than 1% by weight, more preferably less than 0.3% by weight.

In general, any IPDA-containing product mixture which occurs in a process for preparing IPDA may be used. Preference is given to using a product mixture which comprises at least 70% by weight of IPDA, preferably at least 88% by weight of IPDA, more preferably at least 92% by weight of IPDA, most preferably at least 95% by weight of IPDA.

IPDA having a cis/trans isomer ratio of $\leq 66/34$ can be prepared by any known prior art process, which may, for example, have been discussed hereinabove, for preparing IPDA from IPN, $H_2$ and $NH_3$ in the presence of a customary hydrogenation catalyst, for example Ra-nickel, in particular by the processes described in EP-B 0 729 937 and in DE-A 101 42 635, which has an earlier priority date but was unpublished at the priority date of the present application.

Since IPDA having a cis/trans isomer ratio of at least 73/27 is to be obtained, it is only economically viable to fractionally distil product mixtures which comprise IPDA having a cis/trans isomer ratio of less than 73/27. Since IPDA having a cis/trans isomer ratio of less than 70/30 can be prepared using aging catalysts and without a complicated process procedure, the process according to the invention is particularly economical when IPDA having a cis/trans isomer ratio of less than 70/30 is used. It is also possible to use product mixtures which comprise IPDA having a cis/trans isomer ratio of greater than 73/27 in order to even further enrich the cis-isomer by fractional distillation.

Cis-IPDA (having a purity of 98.9%) has a boiling point under atmospheric pressure of 253.4° C., while trans-IPDA (having a purity of 98.4%) has a boiling point under atmospheric pressure of 250.7° C. Since the boiling points of cis- and trans-IPDA are thus close to one another, a special process procedure is necessary in order to obtain IPDA having a cis/trans isomer ratio of at least 73/27.

Steps b and c)

These steps both separate and purify the IPDA-containing product mixture used. Examples of possible components/impurities which are removed in the distillation of the IPDA-containing product mixture (crude IPDA) are $NH_3$, and also the by-products occurring in the preparation of IPDA from IPN such as HCN elimination products, methylated by-products and/or incompletely hydrogenated intermediates.

In step b), the IPDA is firstly fed into the middle region of a (first) distillation column having internals. For this purpose, any desired distillation column can be used. The "middle region" of a distillation column is the region between the top and bottom, i.e. the side feed, of the distillation column.

Useful internals are any internals known to those skilled in the art. Preferred internals are selected from the group of random packings such as Pall rings and Raschig rings, structured sheet metal packings such as Mellapak 250 Y® from Sulzer Ltd. (Winterthur/Switzerland), Montz (Hilden/Germany) and Koch-Glitsch (Wichita, Kans./USA) and structured woven metal packings such as Sulzer BX® from Sulzer Ltd. (Winterthur/Switzerland), Montz (Hilden/Germany) and Koch-Glitsch (Wichita, Kans./USA).

Steps b) and c) can be carried out either in one, two or three columns. It is also possible to use more columns, although generally unnecessary.

When the fractional distillation is carried out in only one column, a dividing wall column is used. When the fractional distillation is carried out in two spatially separated columns, either at least one of the two columns is a dividing wall column or one of the fractions iii) and iv) is obtained at a sidestream takeoff.

When no dividing wall columns are used, preference is given to using three connected conventional distillation columns. This achieves a viable separation and purification.

Preference is given to separating and purifying the IPDA in two columns, of which one is a dividing wall column, and particular preference is given to the second column being a dividing wall column.

When steps b) and c) are carried out in a dividing wall column the low-boiling impurities (fraction i)) are removed via the top of the column and the high-boiling impurities via the bottom of the column. The stream removed at the bottom of the column is only evaporated with the aid of an evaporator. The evaporable fractions are then recycled into the column, while the nonevaporable fractions which are the high-boiling impurities (fraction ii)) are discharged. The corresponding procedure is carried out with the stream withdrawn at the top of the column. This stream is additionally condensed in a condenser and separated in a phase separator. The heavier aqueous phase (fraction ib)), which is wastewater in need of treatment, is discharged, while some of the lighter organic phase (fraction ia)) is recycled into the column for further separation. The desired product of value, the cis-enriched fraction (fraction iii)), is withdrawn on the opposite side of the dividing wall to the feed in the lower region of the column, i.e. above the bottom of the column. The trans-isomer-enriched fraction (fraction iv)) is withdrawn at the opposite side of the dividing wall to the feed in the upper region of the column, i.e. below the top of the column. The dividing wall column is generally operated at bottom temperatures of from 150 to 300° C., preferably from 170 to 250° C., more preferably from 170 to 200° C., and at top temperatures of from 5 to 100° C., preferably from 10 to 90° C., more preferably from 15 to 65° C. The pressure in the column is generally from 10 to 2000 mbar, preferably from 20 to 200 mbar, more preferably from 35 to 50 mbar.

When two columns, one of which is a dividing wall colon, are connected to one another, the dividing wall column may be used either as the fist or the second column. The low-boiling impurities (fraction i)) are removed via the top of the first and/or the second column and the high-boiling impurities (fraction ii)) are removed via the bottom of the first and/or second column. It has proven advantageous to remove the low-boiling impurities via the top of the first column.

As is the case when only one column is used, the stream removed via the top is not condensed until a condenser and is then separated in a phase separator into a heavier aqueous fraction (fraction ib)) and a lighter organic fraction (fraction ia)). Some of the organic fraction (fraction ia)) is recycled into the column for further separation.

When the high-boiling impurities are also removed via the bottom of the first column the IPDA stream which has been substantially freed of low- and high-boiling impurities is withdrawn from the middle region of the first column. When the high-boiling impurities are not removed via the bottom of the first column, the IPDA stream which has been feed of high-boiling impurities is discharged via the bottom of the first column. The stream discharged via the bottom of the column is passed through an evaporator and partially recycled into the column. When the stream discharged via the bottom of the column is the low-boiling impurities and not the IPDA stream, the nonevaporable fractions (fraction ii)) are discharged.

The IPDA stream is then fed into the middle region of the second column. When the low-boiling impurities have not already been removed in the first column, they are now removed via the bottom of the column and discharged.

The desired product of value, the cis-isomer-enriched fraction (fraction iii)), is withdrawn from the side outlet of the second column, i.e. neither at the top nor the bottom, but in the region in between. The trans-isomer enriched fraction (fraction iv)) is removed via the top of the second column or the region below the top, but not the bottom, of the second column.

It is particularly advantageous to withdraw the cis-isomer-enriched fraction (from iii)) from the lower region of the second column and the trans-isomer-enriched fraction (fraction iv)) from the upper region of the second column, and to admix the stream removed from the top and/or bottom of the second column in each case into the crude product stream introduced into the first column, in order to feed this stream/these streams to a renewed separation. As little as possible should be recycled; customarily, from about 1 to 5% by weight of the feed is recycled.

The first column is generally operated at bottom temperatures of from 150 to 300° C., preferably from 170 to 250° C., more preferably from 170 to 200° C., and top temperatures of from 5 to 100° C., preferably from 10 to 90° C., more preferably from 15 to 65° C. The pressure in the first column is customarily from 10 to 1000 mbar, preferably from 30 to 500 mbar, more preferably from 35 to 200 mbar.

The second column is generally operated at bottom temperatures of from 140 to 300° C., preferably from 150 to 250° C., more preferably from 160 to 200° C., and top temperatures of from 100 to 250° C., preferably from 130 to 200° C., more preferably from 140 to 170° C. The pressure in the second column is customarily from 10 to 1000 mbar, preferably from 30 to 300 mbar, more preferably from 35 to 120 mbar.

When three distillation columns are connected to one another, the high-boiling impurities are in each case removed via the bottom of the first, second and/or third column. The bottom discharge is evaporated in an evaporator. The evaporable fractions are recycled into the particular column for renewed separation, and the nonevaporable fractions (fraction ii)) are discharged. Preference is given to discharging the high-boiling impurities via the bottom of the first or the third column. The low-boiling impurities are removed via the top of the first, second and/or third column, condensed in a condenser and then separated in a phase separator into a heavier aqueous fraction (fraction ib)) and a lighter organic fraction (fraction ia)). The heavier aqueous fraction is discharged and the lighter organic reaction is partially recycled into the column and partially discharged. In general, it is possible either to initially remove the low-boiling impurities or initially remove the high-boiling impurities. In general, the low-boiling and high-boiling impurities are not removed in the same column.

Depending on the arrangement of the columns, the cis-isomer-enriched fraction (fraction iii)) is withdrawn either via the top or via the bottom of the second or third column. The trans-isomer-enriched fraction (fraction iv)) is likewise withdrawn either via the top or the bottom of the second or third column. The cis-isomer-enriched and the trans-isomer-enriched fractions may either be withdrawn from the same column, in general the third column, or from different columns. When the two fractions iii) and iv) are withdrawn from the same column, the desired product of value, the cis-isomer-enriched fraction, is withdrawn via the bottom of the column, and the trans-isomer-enriched fraction is withdrawn via the top of the column. When the two fractions iii) and iv) are withdrawn in different columns, it is possible to withdraw both fractions via the top or via the bottom. It is also possible to withdrawn one fraction via the top and the other via the bottom.

In general, the streams withdrawn via the top or bottom of the columns are condensed in a condenser or evaporated in an evaporator and partially recycled into the column for further separation.

When three columns are connected to one another, streams are generally only withdrawn via the top or bottom of the columns, and fed in the middle region between the top and the bottom, i.e. via the side feed of the individual columns.

The three columns are generally operated at bottom temperatures of from 140 to 250° C., preferably from 170 to 225° C., more preferably from 170 to 200° C., and top temperatures of from 40 to 180° C., preferably from 70 to 170° C., more preferably from 70 to 150° C. The pressure in the columns is customarily from 30 to 1500 mbar, preferably from 100 to 500 mbar, more preferably from 110 to 200 mbar.

In one design variant of three columns connected to one another, the low-boiling impurities (fraction i)) are removed in the fist column via the top. The bottom effluent of the first column is fed into the middle region of the second column. The trans-isomer-enriched fraction (fraction iv)) is withdrawn via the top of the second column, while the bottom effluent of the second column is fed into the middle region of the third column for furor separation. The high-boiling impurities (fraction ii)) are then removed via the bottom effluent of the third column, while the desired product of value (fraction iii)) is withdrawn via the top of the third column.

In another design variant of three columns connected in series, the high-boiling impurities (fraction ii)) are removed in the first column via the bottom. The effluent of the first column withdrawn via the top is fed into the middle region of the second column. The low-boiling impurities (fraction i)) are withdrawn via the bottom of the second column, while the bottom effluent of the second column is fed into the middle region of the third column, for further separation. The desired product of value (fraction iii)) is then obtained as the bottom effluent of the third column, while the trans-isomer-enriched fraction (fraction iv)) is withdrawn via the top of the third column.

In a further design variant of three columns connected in series, high-boiling impurities (fraction ii)) are removed in the first column via the bottom. The effluent of the first column withdrawn via the top is fed into the middle region of the second column. The cis-isomer-enriched fraction (fraction iii)) is withdrawn via the bottom of the second column, while the stream withdrawn via the top of the second column is fed into the middle region of the third column for further separation. The trans-isomer-enriched fraction (fraction iv)) is then withdrawn as the bottom effluent of the third column, while the low-boiling impurities (fraction i)) are removed via the top of the third column.

In a fourth design variant of three columns connected in series, the second and third columns are independent of one another. The bottom effluent of the first column is further separated in the third column, while the stream withdrawn via the top is further separated in the second column. Both the bottom effluent and the stream withdrawn via the top are in each case fed into the middle region of the second or third column. The trans-isomer-enriched fraction (fraction iv)) is withdrawn via the bottom of the second column, while the low-boiling impurities (fraction i)) are removed via the top of the second column. The high-boiling impurities (fraction ii)) are then removed via the bottom outlet of the third column, while the desired product of value (fraction iii)) is withdrawn via the top of the third column.

As already illustrated in the description of the arrangement of one, two or three columns, the IPDA is separated by the fractional distillation into at least five fractions—ia), ib), ii), iii) and iv).

The fraction i) which encompasses the subfractions ia) and ib) comprises the low-boiling components/impurities, i.e. the components/impurities which have lower boiling points than trans-IPDA. Fraction i) is in each case removed via the top of the column/s, condensed in a condenser and transferred to a phase separator to separate the organic and aqueous phases. The lighter organic phase (fraction ia)) is then either entirely or partially recycled into the column for further purification and partially discharged. The heavier aqueous phase (fraction ib)) which is wastewater is fed to a waste disposal plant. The amount of IPDA in the wastewater is in general ≦2% by weight, preferably ≦1000 ppm, more preferably ≦200 ppm, based in each case on the total weight of the wastewater (of fraction ib)).

Fraction ii) contains the high-boiling components/impurities, i.e. those components/impurities which have higher boiling points than cis-IPDA. It is in each case removed via the bottom effluent of the columns. The stream removed in this way is fed to an evaporator. The evaporable fractions are recycled back into the column, while the nonevaporable fraction is discharged.

Fraction iii) is the desired product of value. It is thus the cis-IPDA-enriched fraction. Fraction iii) contains IPDA having a cis/trans isomer ratio of ≧73/27, preferably IPDA having a cis/trans isomer ratio in the range from 73/27 to 76/24, more preferably IPDA having a cis/trans isomer ratio in the range from 73/27 to 75/25. Depending on the column or column arrangement, it is withdrawn either via the top, in the upper, middle or lower region or the bottom of the column.

Fraction iv) is the trans-IPDA enriched or cis-IPDA-depleted fraction. It generally contains IPDA having a cis/trans isomer ratio of ≦66/34, preferably IPDA having a cis/tans isomer ratio of ≦63/37, more preferably IPDA having a cis/trans isomer ratio of ≦60/40. Like fraction iii), it is also withdrawn either via the top, in the upper, middle or lower region or the bottom of the column. This fraction can also be utilized commercially (see DE-A 42 11 454).

Design variants according to the invention which are not, however, intended to be limiting will now be described in detail with reference to the plants used for them. The plants are depicted in FIGS. 1 to 7.

The temperatures, pressures and theoretical plates of the individual columns are adapted to the individual design variants of the process. However, it can generally be stated that the average temperatures and pressures in the individual columns are from 5 to 300° C. and from 10 to 2000 mbar respectively, and that the column has an average plate separating performance of from 20 to 120 theoretical plates, preferably from 25 to 80 theoretical plates, more preferably from 30 to 60 theoretical plates.

FIGS. 1 to 7 of the appended drawing show schematic plans in which steps b) and c) of the process according to the invention for obtaining IPDA having a cis/tans isomer ratio of at least 73/27 are carried out in one, two or three columns:

The plants of FIGS. 4 to 7 differ in the arrangement of the columns and thus in the withdrawal points of the fractions: low boiler fraction (ia) and ib)) (4), high boiler fraction ii) (5), cis-isomer-enriched IPDA fraction iii) (2) and trans-isomer-enriched IPDA fraction iv) (3).

Figure 1:
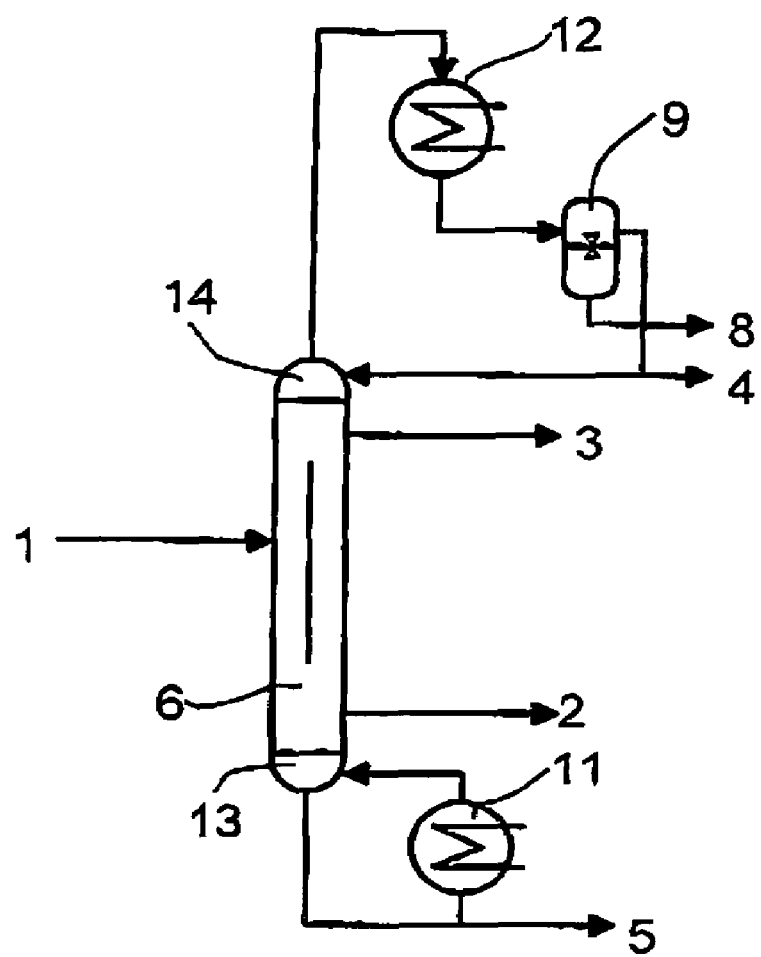
FIG. 1 is a schematic illustration of a plant in which the only column is a dividing wall column.

When a plant according to FIG. 1 is used, the IPDA-containing product mixture is introduced into the middle region of a dividing wall column 6, via an inlet 1. Low-boiling impurities (fraction i)) are removed via the top 14 of the column, condensed in a condenser 12 and transferred after condensation to a phase separator 9. The lighter organic phase (fraction ia)) is partially recycled into column 6, and partially discharged via the outlet 4. The heavier aqueous phase (fraction ib)) is removed via outlet 8 and discarded. High-boiling impurities (fraction ii)) are withdrawn via the bottom 13 of the dividing wall column 6. After evaporation in an evaporator 11, a portion of this bottom effluent is fed back to column 6, and the other portion is discharged via the outlet 5.

The dividing wall column 6 is generally operated at top temperatures of from 5 to 100° C., at bottom temperatures of from 150 to 300° C. and/or at pressures of from 10 to 200 mbar, preferably at top temperatures of from 10 to 90° C., at bottom temperatures of from 170 to 250° C. and/or at pressures of from 20 to 200 mbar, more preferably at top temperatures of from 15 to 65° C., at bottom temperature of from 170 to 200° C. and/or pressures of from 35 to 50 mbar. The separating performance is generally from 1 to 50 theoretical plates, preferably from 1 to 40 theoretical plates, more preferably from 1 to 35 theoretical plates.

Figure 2:
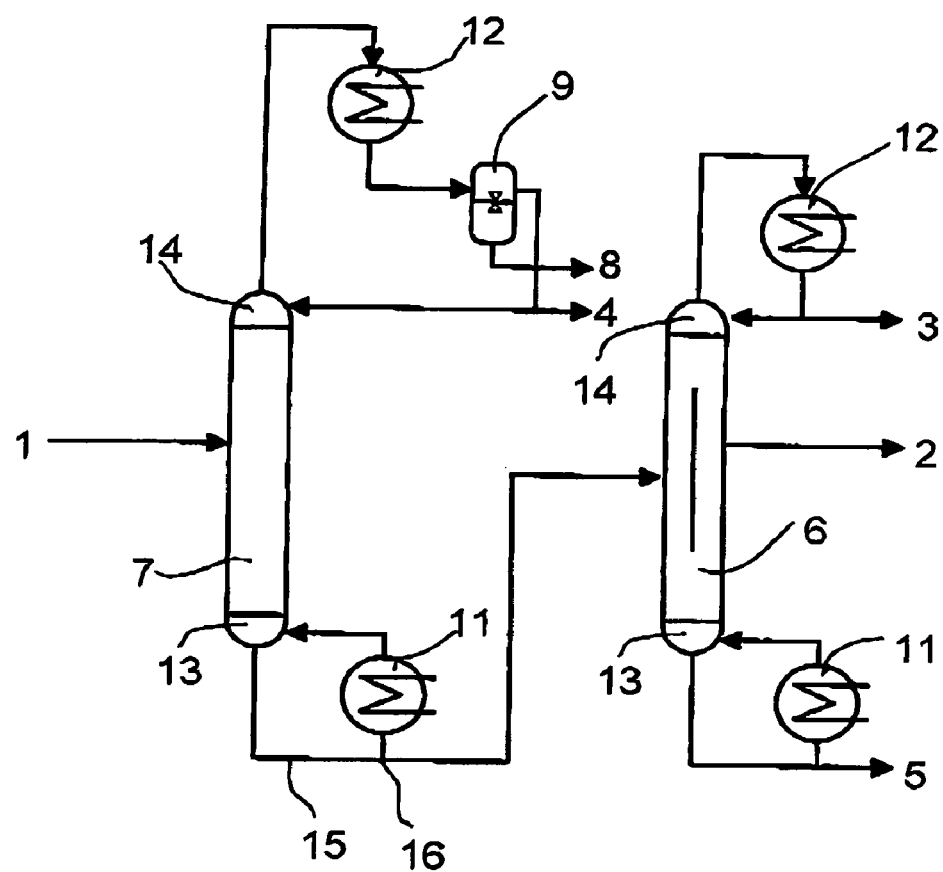
FIG. 2 is a schematic illustration of a plant in which the first column is a conventional distillation column and the second column is a dividing wall column.

In a plant according to FIG. 2, a product mixture comprising IPDA is introduced into a conventional distillation column 7 via an inlet 1 and distilled there. Low-boiling components are removed via the top 14 of the column, transferred to a phase separator 9 after condensation in a condenser 12, and separated there into a lighter organic and a heavier aqueous phase. The lighter organic phase is partially discharged via the takeoff 4, and partially recycled into the distillation column 6. The heavier aqueous phase is discharged via the outlet 8.

The temperatures at the top of the distillation column 7 are generally from 20 to 100° C., preferably from 30 to 80° C. and more preferably from 35 to 65° C., and the bottom temperatures of the distillation column 7 are generally from 150 to 250° C., preferably from 170 to 225° C., more preferably from 170 to 200° C. The average pressure in the column is from 50 to 1500 mbar. Preference is given to an average pressure in the column of from 100 to 500 mbar, particular preference to an average pressure of from 110 to 200 mbar.

The bottoms 13 of the distillation column 7 are transferred continuously to a dividing wall column 6. A branch 16 in line 15 leads to an evaporator 11 where a portion of the bottom effluent is evaporated again and recycled into column 7. The cis-isomer-enriched fraction is withdrawn from column 6 via a sidestream takeoff 2, and the trans-isomer-enriched fraction is removed via the top of the distillation column, condensed in a condenser 12 and then partially recycled into column 6, and partially withdrawn via line 3. High-boiling impurities are removed via the bottom 13 of the dividing wall column 6 and partially discharged via line 5, partially fed back into column 6 after evaporation in an evaporator 11.

The temperatures at the top of the dividing wall column 6 are generally from 100 to 250° C., preferably from 130 to 190° C. and more preferably from 140 to 160° C., and the bottom temperatures of the dividing wall column 6 are generally from 150 to 300° C., preferably from 170 to 250° C., more preferably from 170 to 195° C. The average pressure in the column is from 10 to 1000 mbar. Preference is given to an average pressure in the column of from 30 to 200 mbar, particular preference to an average pressure of 35 to 50 mbar.

Figure 3:
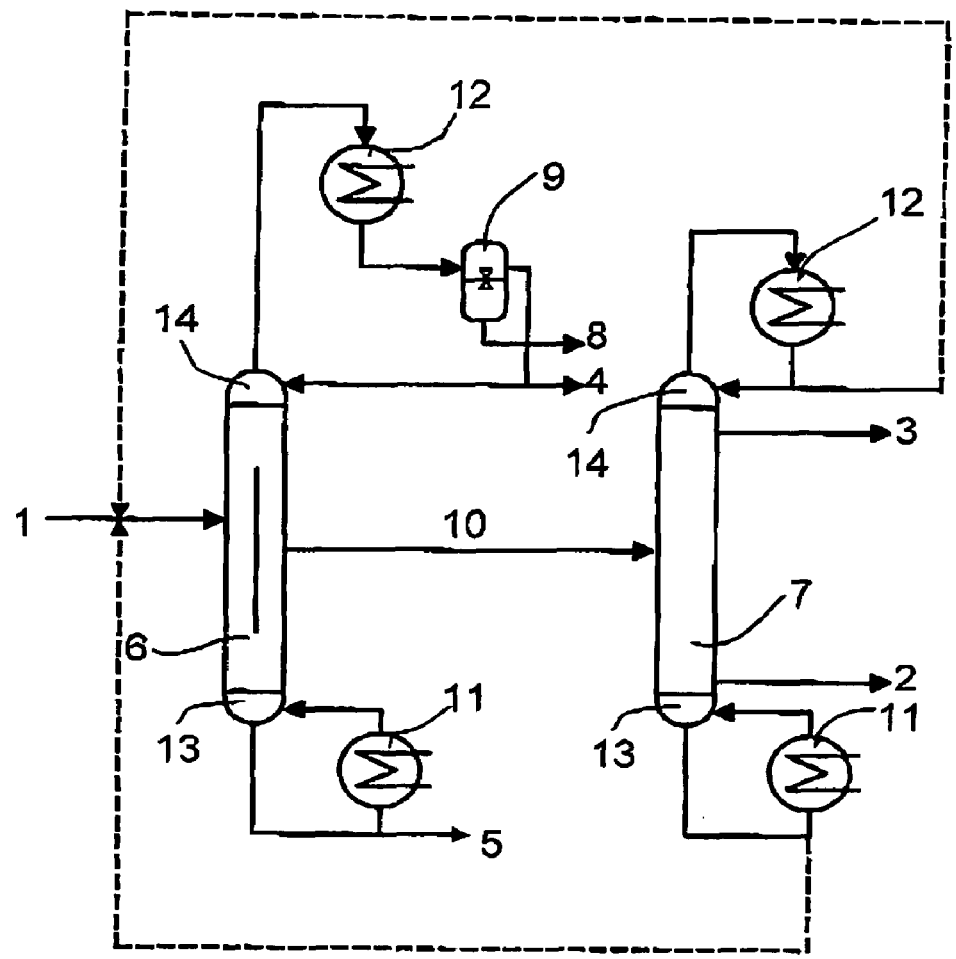
FIG. 3 is a schematic illusion of a plant in which the first column is a dividing wall column and the second column is a conventional distillation column.

When step b) of the process according to the invention is carried out in a plant according to FIG. 3, the IPDA is introduced into a dividing wall column 6 via the feed 1. High-boiling impurities are removed from the column as bottoms 13 and partially discharged via the outlet 5, partially fed back to the column after the evaporation in an evaporator 11. Low-boiling impurities are removed from the column via the top 14 and transferred to a phase separator 9 after condensation in a condenser 12. The lighter organic phase which has collected is partially discharged via the outlet 4, partially recycled into the dividing wall column 6. The heavier phase is discharged via the outlet 8.

The temperatures at the top of the dividing wall column 6 are generally from 5 to 100° C., preferably from 10 to 90° C. and more preferably from 15 to 50° C., and the bottom temperatures of the dividing wall column 6 are generally from 150 to 300° C., preferably from 170 to 250° C., more preferably from 170 to 195° C. The average pressure in the column is from 10 to 1000 mbar. Preference is given to an average pressure in the column of from 30 to 200 mbar, and particular preference to an average pressure of from 35 to 50 mbar.

The purified IPDA is withdrawn via a sidestream takeoff 10 of the dividing wall column 6 and is transferred to a further column 7 which is in this case configured as a conventional distillation column.

The temperatures at the top of the distillation column 7 are generally from 130 to 250° C., preferably from 140 to 200° C. and more preferably from 150 to 170° C., and the bottom temperatures of the distillation column 7 are generally from 140 to 250° C., preferably from 150 to 220° C., more preferably from 160 to 190° C. The average pressure in the column is from 30 to 1000 mbar. Preference is given to an average pressure in the column of from 50 to 300 mbar, particular preference to an average pressure of from 80 to 120 mbar.

The lowest-boiling components are removed from column 7 via the top 14 and, after condensation in a condenser 12, partially recycled to column 7, and partially introduced into feed 1, in order to feed it to a renewed separation in column 6. The same happens to the highest-boiling components which are removed from column 7 via the bottom 13 and partially fed back into column 7 after evaporation in an evaporator 11, and partially added to the product mixture in feed 1.

The cis-isomer enriched fraction is removed via a sidestream takeoff 2, and the trans-isomer-enriched fraction via a sidestream takeoff 3. The sidestream takeoff for the cis-isomer-enriched fraction is below the sidestream takeoff for the tans-isomer-enriched fraction.

The performance of step b) of the process in a plant according to FIG. 3 is particularly advantageous, since low- and high-boiling impurities are each removed at two points: low-boiling components are removed both via the top 14 of column 6 and via the top 14 of column 7, while high-boiling impurities are removed both via the bottom effluent 13 of column 6 and via the bottom effluent 13 of column 7.

When step b) of the process according to the invention is carried out in plants according to FIG. 4, 5, 6 or 7, three conventional distillation columns 7, 7A and 7B are used in each case which differ in the geometric details—the diameter and the height.

The temperatures at the tops of distillation columns 7, 7A and 7B are generally from 40 to 180° C., preferably from 70 to 170° C., more preferably from 70 to 150° C., and the temperatures at the bottoms are customarily from 150 to 250° C., preferably from 170 to 225° C., more preferably from 170 to 190° C. The pressure in these columns is generally from 30 to 1500 mbar, preferably from 100 to 500 mbar, more preferably from 110 to 200 mbar.

Figure 4:
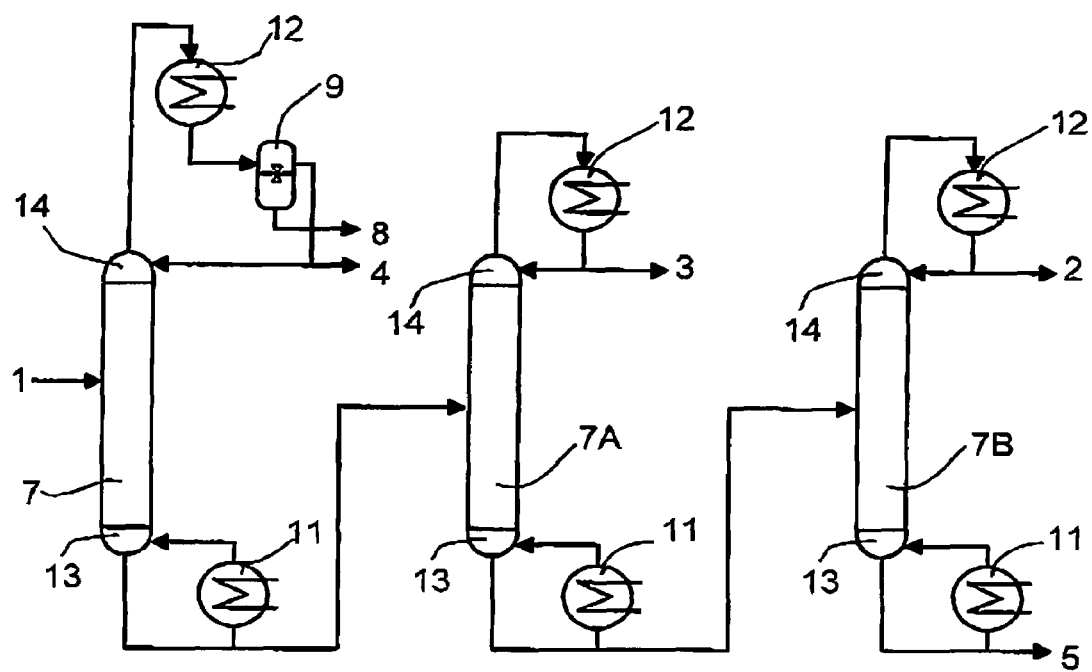
FIGS. 4 to 7 are schematic illustrations of a plant in which all three columns are conventional distillation columns.

When the process is carried out in a plant according to FIG. 4, the IPDA-containing product mixture is introduced into the middle region of the first column 7 via a feed 1. Low-boiling impurities are removed via the top of the column, condensed in a condenser 12 and then transferred to a phase separator 9. The lighter organic phase is partially recycled into column 7, partially discharged via outlet 4. The heavier aqueous phase is removed via the outlet 8 and discarded. The IPDA purified in this way which may still contain high-boiling impurities is removed via the bottom of the fist column 7 and fed into the middle region of the second column 7A. The trans-isomer-enriched fraction is now removed from the top of the second column 7A, condensed in a condenser, partially removed via line 3 and partially recycled into column 7A. The cis-isomer-enriched fraction which may still contain high-boiling impurities is removed via the bottom of column 7A and fed into the middle region of the third column 7B. High-boiling impurities are now discharged via the bottom of the third column via the outlet 5. The cis-isomer-enriched fraction is withdrawn via the top of the column 7B, condensed in a condenser 11 and then partially withdrawn via the line 2, partially fed back into column 7B for renewed separation.

Figure 5:
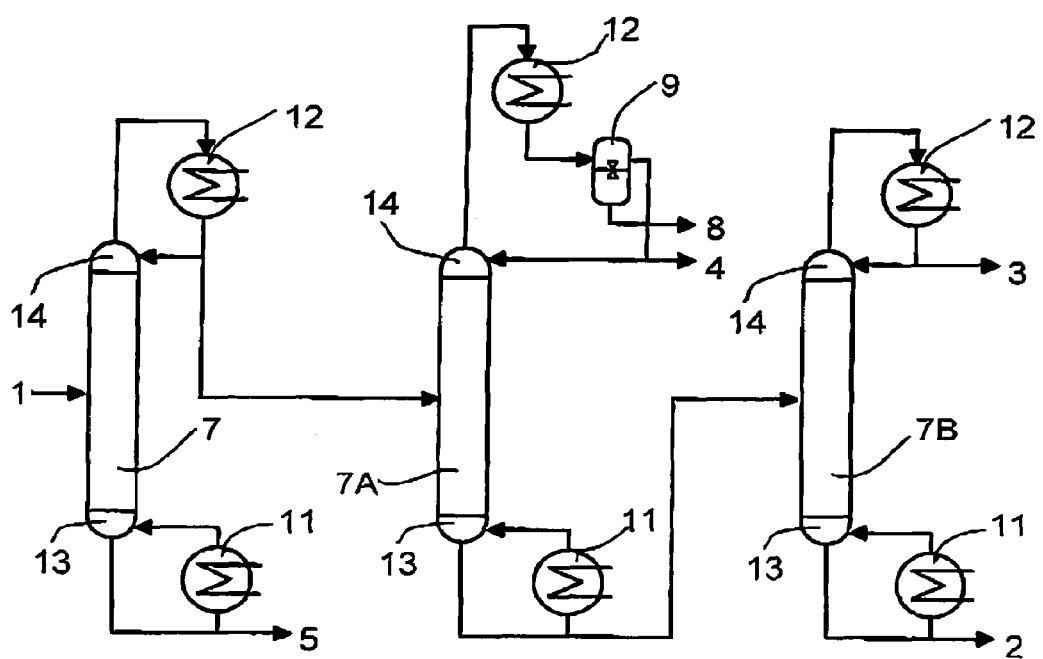

When the process is carried out in a plant according to FIG. 5, the IPDA-containing product mixture is introduced into the middle region of the first column 7 via an inlet 1. High-boiling impurities are now withdrawn via the bottom of this first column and condensed in a condenser 11 and then the less volatile constituents are discharged via the outlet 5 and the more volatile fractions are recycled into column 7 for renewed separation. The IPDA-containing fraction purified in this way is removed via the top of column 7, condensed in a condenser 11, partially recycled into column 7 and partially introduced into the middle region of the second column 7A. Low-boiling impurities are removed via the top of this second column 7A, condensed in a condenser 11 and then transferred to a phase separator 9. The lighter organic phase is partially recycled into column 7A, partially discharged via outlet 4. The heavier aqueous phase is removed via the outlet 8 and discarded. The IPDA purified in this way is then removed via the bottom of the second column 7A and fed into the middle region of the third column 7B for further separation of cis- and trans-IPDA. The cis-isomer-enriched fraction is removed via the bottom of column 7B and condensed in a condenser 11. The less volatile constituents which are the cis-isomer are discharged via the outlet 2, and the more volatile constituents are fed back into column 7B for renewed separation.

Figure 6:
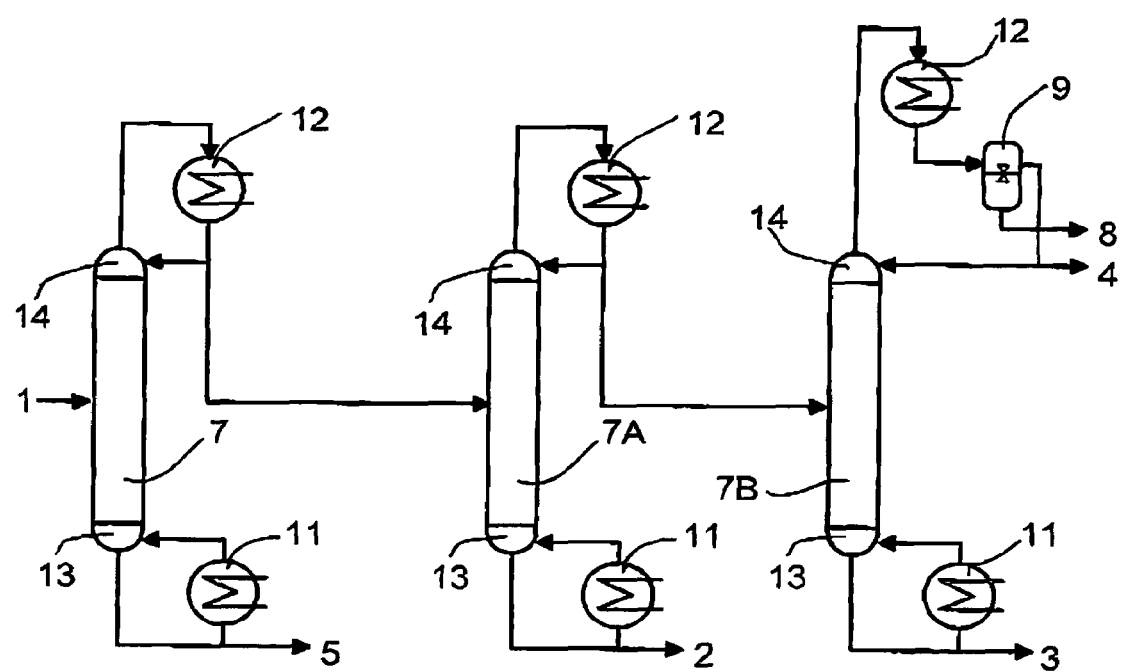

When the process is carried out in a plant according to FIG. 6, the IPDA-containing product mixture is introduced into the middle region of the first column 7 via an inlet 1. Low-boiling impurities are removed from column 7 via the top 14 and condensed in a condenser 12. A portion is then recycled into column 7, and the other portion introduced into the middle region of the second column 7A for further separation. Bottom effluent is continuously withdrawn from the bottom 13 of the first column 7 and partially discharged via line 5 (fraction ii)), partially recycled back into column 7 after evaporation in the evaporator 11. The trans-isomer-enriched fraction which still contains low-boiling components/impurities is now removed via the top 14 of the second column 7A, condensed in a condenser 12 and partially fed into the middle region of the third column 7B, partially recycled into column 7A. The cis-isomer-enriched fraction (fraction iii)) is removed via the bottom 13 of column 7A or fed back to column 7A after evaporation in an evaporator 11. Low-boiling impurities are now withdrawn via the top 14 of the third column 7B, condensed in a condenser 12 and then introduced into a phase separator. The lighter organic phase (fraction ia)) is partially withdrawn via the line 4, partially fed back into column 7B for renewed separation. The heavier aqueous phase (fraction ib)) is discharged via the outlet 8. The trans-isomer-enriched fraction is withdrawn via the bottom 13 of column 7B, and partially evaporated in an evaporator 11 and fed back to column 7B, partially discharged via the line 3.

Figure 7:
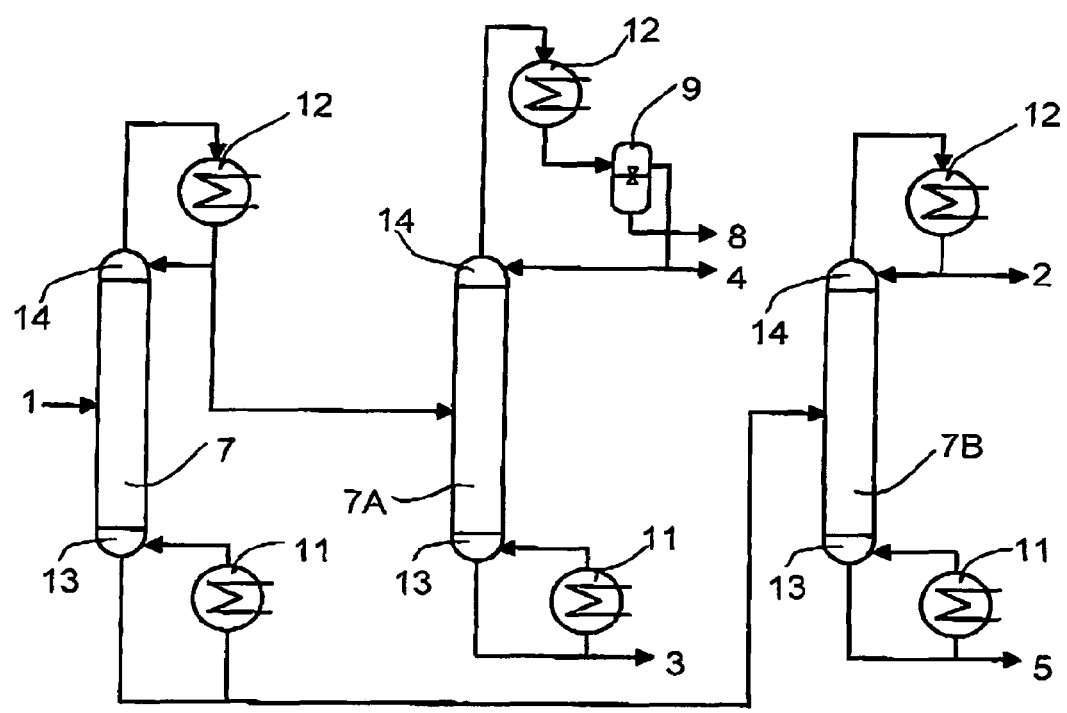

When the process is carried out in a plant according to FIG. 7, the IPDA-containing product mixture is introduced via line 1 into the middle region of the first column 7. The lower-boiling fraction of the product mixture is removed via the top 14 of column 7, condensed in a condenser 12 and then partially transferred to the second column 7A, partially recycled into column 7. The higher-boiling fraction of the product mixture is withdrawn via the bottom effluent 13 of column 7. It is partially evaporated in the evaporator 11 and recycled back into column 7, partially introduced into the middle region of the third column 7B.

In the second column the low boiler fraction (fraction i)) and the trans-isomer-enriched fraction (fraction iv)) are separated. The low-boiling components/impurities (fraction i)) are removed via the top 14 of the second column 7A, condensed in a condenser 12 and transferred to a phase separator 9. The lighter organic phase (fraction ia)) is partially discharged via line 4, partially recycled in column 7A. The heavier aqueous phase (fraction ib)) is withdrawn via line 8. The trans-isomer-enriched fraction is removed via the bottom 13 of the second column 7A, and partially evaporated again in an evaporator 11 and recycled into column 7A, partially removed via line 3.

In the third column, the high boiler fraction (fraction ii)) and the cis-isomer-enriched fraction (fraction iii)) are separated. High-boiling impurities are removed via the bottom of the third column and partially discharged via the outlet 5, partially recycled back into column 7B after evaporation in an evaporator 11. The cis-isomer-enriched fraction is withdrawn via the top of column 7B, condensed in a condenser 12 and then partially withdrawn via line 2, partially recycled into column 7B for renewed separation.

The invention is now additionally illustrated in more detail in the implementation examples which follow.

IMPLEMENTATION EXAMPLES

In the implementation examples, the distillation of crude IPDA having the composition reported in Table 1 was investigated. The required product purities for the trans-IPDA- and cis-IPDA-enriched fractious obtained in this way can likewise be taken from Table 1. In addition, the high boiler removal and low boiler removal should result in a maximum of 0.5 kg/h of IPDA (cis and trans) being lost in the low boiler and wastewater stream, and a maximum of 10 kg/h of IPDA (cis and trans) being lost in the high boiler stream.

All implementation examples have been calculated using the simulation software CHEMASIM from BASF AG. The apparatus has been dimensioned using the design programs of BASF AG. The materials data of the system considered have been checked with the aid of subsequent calculations on the apparatus present.

TABLE 1

Composition of the crude IPDA to be distilled and required purity of the fractions obtainable in this way

|  | crude IPDA | trans-IPDA-enriched fraction | cis-IPDA-enriched fraction |
| --- | --- | --- | --- |
| water | 9.5% by weight | 250 ppm | 250 ppm |
| low boilers | 4.5% by weight | <250 ppm | <250 ppm |
| trans-IPDA | 26.1% by weight | $\geq$43% by weight | $\leq$24% by weight |
| cis-IPDA | 55.5% by weight | $\leq$57% by weight | $\geq$76% by weight |
| high boilers | 4.4% by weight | <50 ppm | <50 ppm |
| cis/trans isomer ratio | 68/32 | 57/43 | 76/24 |
| amount distilled/obtained | 2160 kg/h | 430 kg/h | 1320 kg/h |

Example 1

Performance of the Process According to the Invention in a Plant According to FIG. 4

2160 kg/h of an IPDA-containing product mixture are introduced into the first column 7 via a feed 1 to the $15^{th}$ of 28 trays. Low-boiling impurities are removed via the top of the column and condensed in a condenser 12 which is operated at a temperature of 45° C. The condensate is then transferred to a phase separator 9. The lighter organic phase is partially recycled into column 7, partially removed (in an amount of 108 kg/h). The heavier aqueous phase is removed in an amount of 175 kg/h and fed to wastewater treatment. The proportion of IPDA in the organic and aqueous phases removed is 0.5 kg/h.

The IPDA purified in this way which contains <55 ppm of low-boiling impurities is removed via the bottom of the first column 7 and fed to the $10^{th}$ of 31 trays of the second column 7A. The trans-isomer-enriched fraction is now removed via the top of the second column 7A, condensed in a condenser, partially removed via line 3 (in an amount of 434 kg/h having a trans-IPDA content of 43.2% and a low boiler content of <250 ppm) and partially recycled in column 7A. The cis-isomer-enriched fraction which may still contain high-boiling impurities is withdrawn in an amount of 1421 kg/h via the bottom of column 7A and fed to the $10^{th}$ of 20 trays of the third column 7B. High-boiling impurities are now discharged via the outlet 5 in an amount of 105 kg/h via the bottom of the third column, and the proportion of IPDA is <10 kg/h. The cis-isomer-enriched fraction is withdrawn via the top of column 7B, condensed in a condenser 11 and then partially withdrawn via line 2 (in an amount of 1316 kg/h having a cis content of 76% and a proportion of high boiler of <50 ppm), partially fed back into column 7B for renewed separation.

Details on the temperature and pressure conditions in the columns 7, 7A and 7B, the reflux ratios required for the separation, and also their internals and dimensions can be taken from Table 2.

TABLE 2

Characteristic data of the columns 7, 7A and 7B:

|  | Column 7 | Column 7A | Column 7B |
|---|---|---|---|
| Diameter [mm] | 900 | 1400 | 1100 |
| Height [m] | 22 | 19 | 16 |
| Pressure at the top of the column [mbar] | 100 | 100 | 35 |
| Temperature at the top of the column [° C.] | 87 | 167 | 140 |
| Temperature at the bottom of the column [° C.] | 170 | 174 | 176 |
| Reflux ratio | 3.1 | 14.9 | 1.05 |
| Heating output at the bottom of the column [kW] | 277 | 615 | 222 |
| Internals in the rectifying section of the column | 2 × 3.5 m sheet metal packing of 250 m$^2$/m$^3$ | 2 × 4.0 m sheet metal packing of 250 m$^2$/m$^3$ | 1 × 4.0 m sheet metal packing of 250 m$^2$/m$^3$ |
| Internals in the stripping section of the column | 2 × 3.5 m sheet metal packing of 250 m$^2$/m$^3$ | 1 × 4.0 m sheet metal packing of 250 m$^2$/m$^3$ | 1 × 4.0 m sheet metal packing of 250 m$^2$/m$^3$ |

Example 2

Performance of the Process According to the Invention in a Plant According to FIG. 2

2160 kg/h of a product mixture containing IPDA are introduced via an inlet 1 to the 15$^{th}$ tray of 28 trays of a column 7 which corresponds to the column 7 described in Example 1, i.e. the characteristic data and the operating conditions are the same. Low-boiling components are removed via the top 14 of column 7, transferred after condensation in a condenser 12 to a phase separator 9 and separated there into a lighter organic and a heavier aqueous phase. The lighter organic phase is partially (in an amount of 108 kg/h) discarded via the takeoff 4, partially recycled into the distillation column 6. The heavier aqueous phase is disposed of in an amount of 175 kg/h via the takeoff 8, and the proportion of IPDA in the removed streams is 0.5 kg/h.

The bottoms 13 of the distillation column 7 containing a mixture of high boilers and cis- and trans-IPDA are continuously transferred to a dividing wall column 6, specifically to the 15$^{th}$ of 44 trays on the feed side. The cis-isomer-enriched fraction is withdrawn via a sidestream takeoff 2 of the column 6 in an amount of 1320 kg/h having a cis content of 76% and a high boiler content below 50 ppm, and the trans-isomer-enriched fraction is removed via the top of the distillation column and condensed in a condenser 12 which is operated at 139° C. The condensate is then partially recycled into column 6, partially withdrawn via line 3 in an amount of 430 kg/h at a tans content of 57%. High-boiling impurities are removed via the bottom 13 of the dividing wall column 6 and partially discharged via line 5 (in an amount of 104 kg/h having an IPDA content of <10 kg/h), partially fed back to column 6 after evaporation in an evaporator 11.

Details on the temperature and pressure conditions in columns 7 and 6, the reflux ratios required for the separation, and also their internals and dimensions can be taken from Table 3.

TABLE 3

Characteristic data of columns 7 and 6 (dividing wall column):

|  | Column 7 | Column 6 |
|---|---|---|
| Diameter [mm] | 900 | 1600 |
| Height [m[ | 22 | 19 |
| Pressure at the top of the column [mbar] | 100 | 35 |
| Temperature at the top of the column [° C.] | 87 | 139 |
| Temperature at the bottom of the column [° C.] | 170 | 185 |
| Reflux ratio | 0.46 | 13.4 |
| Heating output at the bottom of the column [kW] | 277 | 547 |
| Division ratio of liquid above dividing wall; feed side: takeoff side |  | 0.436:1 |
| Division ratio of vapor below dividing wall; feed side: takeoff side |  | 0.7:1 |
| Internals in the rectifying section of the column | 2 × 3.5 m sheet metal packing of 250 m$^2$/m$^3$ | 1 × 4.0 m woven metal packing of 500 m$^2$/m$^3$ |
| Dividing wall region internals Feed side/takeoff side above feed/takeoff |  | Feed side: 1 × 1.5 m woven metal packing of 500 m$^2$/m$^3$; Takeoff side: 1 × 3.0 m woven metal packing of 500 m$^2$/m$^3$ |
| Dividing wall region internals Feed side/takeoff side below feed/takeoff |  | Feed side: 1 × 3.75 m woven metal packing of 500 m$^2$/m$^3$; Takeoff side: 1 × 2.25 m woven metal packing of 500 m$^2$/m$^3$ |
| Internals in the stripping section of the column | 2 × 3.5 m sheet metal packing of 250 m$^2$/m$^3$ | 1 × 1.75 m woven metal packing of 500 m$^2$/m$^3$ |

Example 3

Performance of the Process According to the Invention in a Plant According to FIG. 1

When a single dividing wall column is used this column combines the removal of the low boilers and the water at the top of the column with the removal of the high boilers at the bottom of the column and the enrichment of the cis-isomer. Therefore, two sidestream takeoffs are provided on the takeoff side of the dividing wall. The trans-IPDA-enriched fraction is removed at the upper sidestream takeoff, and the cis-isomer-enriched fraction at the lower sidestream takeoff.

2160 kg/h of an IPDA-containing product mixture are introduced via a line 1 to the 15$^{th}$ tray of 75 trays of the dividing wall column 6. Low-boiling impurities are removed via the top 14 of the column and condensed in a condenser 12 which is operated at a temperature of 17° C. The condensate is then transferred to a phase separator 9. The lighter organic phase is partially recycled in column 6, partially discharged via the outlet 4 (in an amount of 108 kg/h), and the proportion of IPDA is <0.5 kg/h. The heavier aqueous phase is removed via the outlet 8 in an amount of 175 kg/h and fed to wastewater treatment. High-boiling impurities are removed in an amount of 105 kg/h via the bottom 13 of the dividing wall column 6, and the IPDA content is <10 kg/h. The cis-isomer-enriched fraction is withdrawn in an amount of 1320 kg/h at the height of the 14$^{th}$ tray on the takeoff side at a cis/tans isomer ratio of 76/34 and a high boiler content of <50 ppm. The trap-isomer-enriched fraction is withdrawn in an amount of 430 kg/h at the height of the 60$^{th}$ tray on the takeoff side at a cis/trans isomer ratio of 57/43 and a proportion of low boilers of <250 ppm.

Details on the temperature and pressure ratios in column 6, the reflux ratios required for the separation, and also their internals and dimensions can be taken from table 4.

Reference numeral list

| | |
|---|---|
| 1 | IPDA feed |
| 2 | Takeoff for the cis-isomer-enriched fraction |
| 3 | Takeoff for the trans-isomer-enriched fraction |
| 4 | Takeoff for low-boiling impurities (organic fraction) |
| 5 | Takeoff for high-boiling impurities |
| 6 | Dividing wall column |
| 7, 7A, 7B | Distillation column |
| 8 | Takeoff for the heavier constituents of the low boiler fraction; takeoff for the wastewater in need of treatment |
| 9 | Phase separator |
| 10 | Sidestream takeoff |
| 11 | Evaporator |
| 12 | Condensor |
| 13 | Bottom of the column |
| 14 | Top of the column |
| 15 | Line |
| 16 | Branch |

We claim:

1. A process for recovering 3-aminomethyl-3,5,5-trimethylcyclohexylamine (isophoronediamine, IPDA) having a fractionally distilled cis/tran isomer ratio of at least 73/27, which comprises the following steps:
   a. providing IPDA in a cis/tran isomer ratio of <73/27; and
   b. feeding IPDA into the middle region of a distillation column having internals and distilling the IPDA in this distillation column at a temperature of from 5 to 300° C. and a pressure of from 10 to 2000 mbar; and
   c. optionally further distilling the IPDA obtained by step b) in at least one further column, and thus further purifying the IPDA;

TABLE 4

Characteristic data of column 6 (dividing wall column):

| | Column 6 |
|---|---|
| Diameter [mm] | 2100 |
| Height [m] | 32 |
| Pressure at the top of the column [mbar] | 20 |
| Temperature at the top of the column [° C.] | 63 |
| Temperature at the bottom of the column [° C.] | 175 |
| Reflux ratio | 10.61 |
| Heating output at the bottom of the column [kW] | 920 |
| Division ratio of liquid above dividing wall; feed side: takeoff side | 0.4:1 |
| Division ratio of vapor below dividing wall; feed side: takeoff side | 1:1 |
| Internals in the rectifying section of the column | 1 × 2.5 m woven metal packing of 500 m$^2$/m$^3$ |
| Dividing wall region internals feed side/takeoff side above feed/first takeoff | Feed side: 3 × 3.5 m woven metal packing of 500 m$^2$/m$^3$; Takeoff side: 1 × 1.25 m woven metal packing of 500 m$^2$/m$^3$ |
| Dividing wall region internals takeoff side between first and second takeoff | 2 × 4.0 m, 1 × 3.0 m woven metal packing of 500 m$^2$/m$^3$ |
| Dividing wall region internals feed side/takeoff side below feed/second takeoff | Feed side: 1 × 3.75 m woven metal packing of 500 m$^2$/m$^3$; Takeoff side: 1 × 2.0 in woven metal packing of 500 m$^2$/m$^3$ |
| Internals in the stripping section of the column | 1 × 1.5 m woven metal packing of 500 m$^2$/m$^3$ | where steps b) and optionally c) separate the IPDA used in step a) into at least five fractions ia) to iv):

ia) an organic proportion of a fraction of impurities having lower boiling points than trans-IPDA, ib) an aqueous proportion of a fraction of impurities having lower boiling points than trans-IPDA, ii) a fraction of impurities having higher boiling points than cis-IPDA, iii) an IPDA fraction having a cis/trans isomer ratio of $\geq 73/27$ and iv) a depleted IPDA fraction having a cis/trans isomer ratio of $\leq 66/34$.

2. A process as claimed in claim 1, wherein the proportion of cis- and trans-IPDA in the fraction ib) obtained by steps b) and c) is $\leq 2\%$ weight, based on the total weight of fraction ib).

3. A process as claimed in claim 2, wherein IPDA is used in step a) which has a cis/trans isomer ratio of <70/30.

4. A process as claimed in claim 3, wherein said IPDA is used in step iii) which has a cis/trans isomer ratio of 73/27 to 75/25.

5. A process as claimed in claim 4, wherein said depleted IPDA is used in step iv) which has a cis/trans isomer ratio of $\leq 66/34$.

6. A process as claimed in claim 5, wherein the distillation column used in step b) has a separating performance of at least 20 theoretical plates.

7. A process as claimed in claim 6, wherein at least said distillation column or said at least one further column is a dividing wall column.

8. A process as claimed claim 6, wherein said distillation column and said at least one further column are used, of which one is a dividing wall column.

9. A process as claimed in claim 6, wherein said distillation column or one further column are used and one of the fractions iii) or iv) is removed at a sidestream takeoff.

10. A process as claimed in claim 1, wherein IPDA is used in step a) which has a cis/trans isomer ratio of <70/30.

11. A process as claimed in claim 1, wherein the distillation column used in step b) has a separating performance of at least 20 theoretical plates.

12. A process as claimed in claim 1, wherein at least said distillation column or said at least one further column is a dividing wall column.

13. A process as claimed claim 1, wherein said distillation column and said at least one further column are used, of which one is a dividing wall column.

14. A process as claimed in claim 1, wherein said distillation column and one further column are used and one of the fractions iii) or iv) is removed at a sidestream takeoff.

15. A process as claimed in claim 1, wherein said at least one further column is two further columns and said distillation column and said two further columns are connected to one another.

16. A process as claimed in claim 1, wherein the internals in the distillation column or the at least one further column used in steps b) and/or c) are selected from the group consisting of random packings, sheet metal structured packings and woven metal structured packings.

17. A process as claimed in claim 1, wherein said IPDA is used in step iii) which has a cis/trans isomer ratio of 73/27 to 75/25.

18. A process as claimed in claim 1, wherein said depleted IPDA is used in step iv) which has a cis/trans isomer ratio of $\leq 66/34$.

* * * * *

UNITED STATES PATENT AND TRADEMARK OFFICE
CERTIFICATE OF CORRECTION

PATENT NO. : 7,497,931 B2  
APPLICATION NO. : 10/524084  
DATED : March 3, 2009  
INVENTOR(S) : Frank Funke et al.

It is certified that error appears in the above-identified patent and that said Letters Patent is hereby corrected as shown below:

Title Page:

The last 4 lines of the Abstract reads, "v) and IPDA fraction having a cis/trans isomer ratio of $\geq 73/27$ and vi) a depleted IPDA fraction having a cis/trans isomer ratio of $\leq 66/34$." – and should read – "iii) an IPDA fraction having a cis/trans isomer ratio of $\geq 73/27$ and iv) an IPDA fraction having a cis/trans isomer ratio of $\leq 66/34$."

Signed and Sealed this

Sixteenth Day of June, 2009

JOHN DOLL  
*Acting Director of the United States Patent and Trademark Office*